United States Patent [19]
Fukuhara

[11] Patent Number: 5,529,582
[45] Date of Patent: Jun. 25, 1996

[54] APPARATUS FOR INSERTING LARYNGEAL MASK

[76] Inventor: Tomio Fukuhara, 19-3, Honamanuma 1-chome, Suginami-ku, Tokyo, Japan

[21] Appl. No.: 188,939

[22] Filed: Feb. 1, 1994

[51] Int. Cl.⁶ .................................................. A61B 17/00
[52] U.S. Cl. ................................................................ 606/205
[58] Field of Search ................................. 606/205–211; 294/99.2

[56] References Cited

U.S. PATENT DOCUMENTS

| | | | |
|---|---|---|---|
| 4,024,870 | 5/1977 | Sandel | 606/207 |
| 4,944,741 | 7/1990 | Hasson | 606/206 |

FOREIGN PATENT DOCUMENTS

| | | | |
|---|---|---|---|
| 0187264 | 7/1907 | Germany | 606/207 |

OTHER PUBLICATIONS

Br. J. Anaesth. vol. 55 published in 1983, pp. 801–805, titled "The Laryngeal Mask–A New Concern In Airway Management" by A. I. J. Brain.
Anaesthesia. vol. 40 published in 1985, pp. 356–361, titled "The Laryngeal Mask Airway" (Development and preliminary trials of a new type of airway) by A. I. J. Brain.
Anaesthesia. vol. 44 published in 1989, pp. 238–241, titled "The Laryngeal Mask Airway" (A study of 100 patients during spontaneous breathing) by P. M. Brodrick et al.
Anaesthesia. vol. 48 published in 1993, p. 80, titled "A 'skid' for easier insertion of the laryngeal mask airway" by J. B. Harding.

Primary Examiner—Gary Jackson
Assistant Examiner—William W. Lewis
Attorney, Agent, or Firm—Armstrong, Westerman, Hattori, McLeland & Naughton

[57] ABSTRACT

An apparatus for inserting a laryngeal mask has a holder portion, a pair of clamp bars which extend forwards from the holder portion and which are adapted to hold therebetween in a pinching manner a tube connecting portion provided on an outside surface of the laryngeal mask. The pair of clamp bars are connected together at their front ends to thereby form an abutment portion which is adapted to abut a front end of the outside surface of the laryngeal mask. The apparatus also has a band piece which extends from the abutment portion along the clamp bars towards the holder portion and which can be pulled towards the holder portion. Another apparatus for inserting a laryngeal mask has a pair of clamp bars which are arranged to hold therebetween a tube connecting portion provided on an outside surface of the laryngeal mask, a pivot pin for pivotally supporting the clamp bars at approximately intermediate portions thereof such that front ends and rear ends of the clamp bars can respectively move towards and away from each other, and an abutment portion which is formed at the front ends of the clamp bars so as to abut a front end of the outside surface of the laryngeal mask.

9 Claims, 4 Drawing Sheets

FIG. 1B
FIG. 1A
FIG. 1C
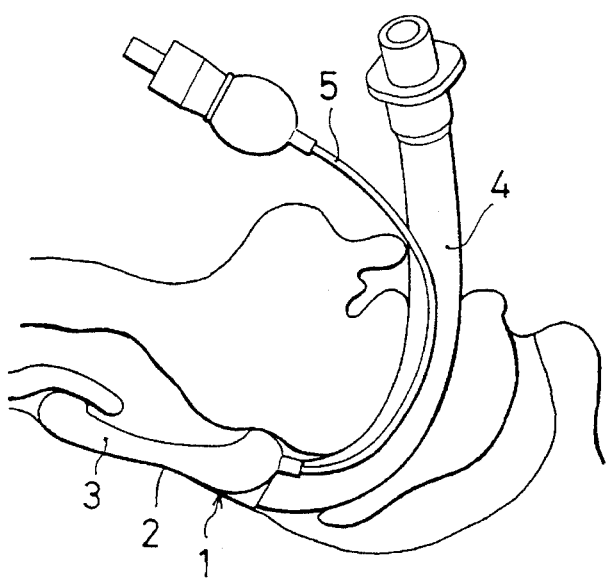
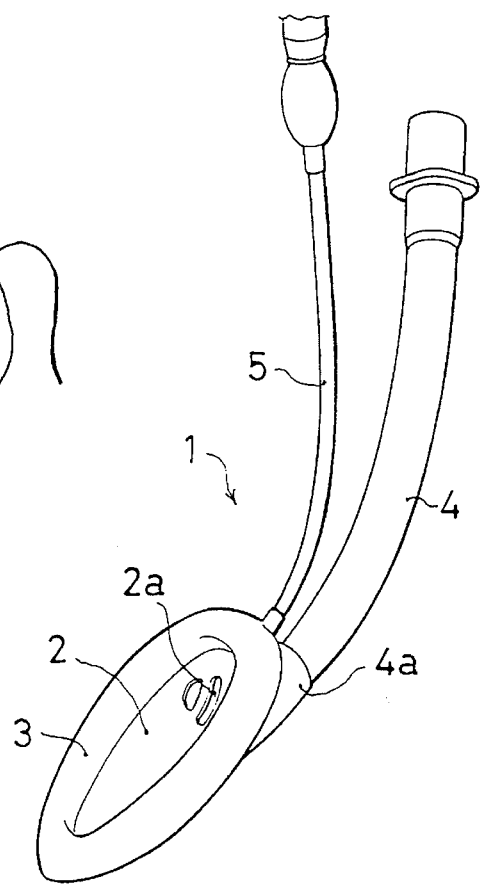
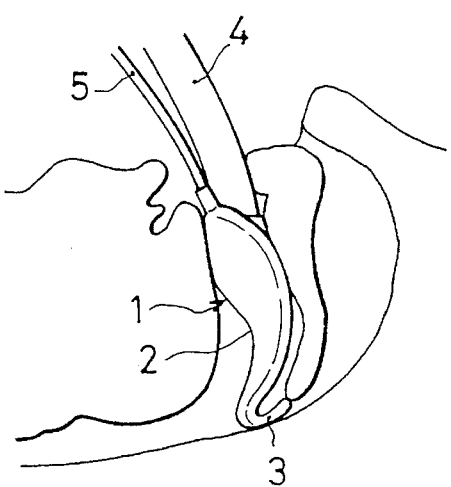

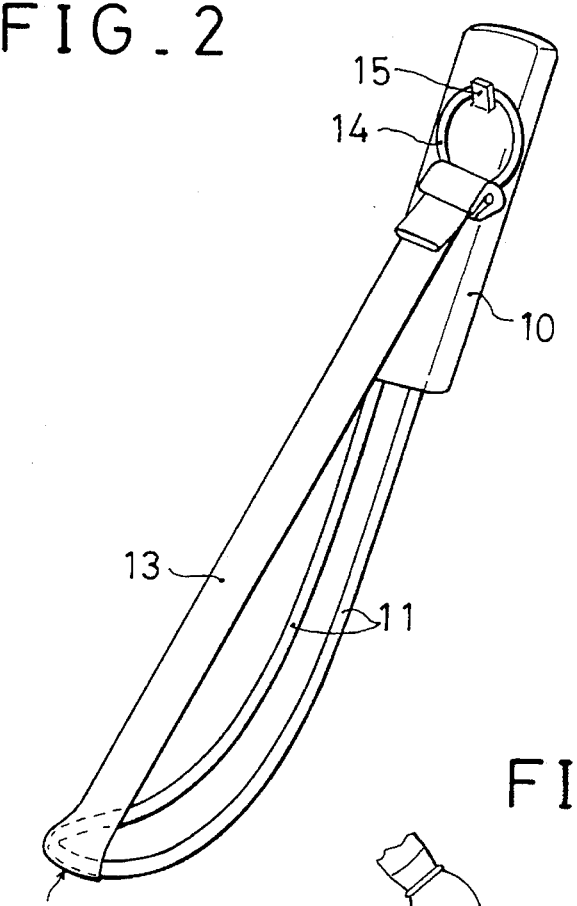
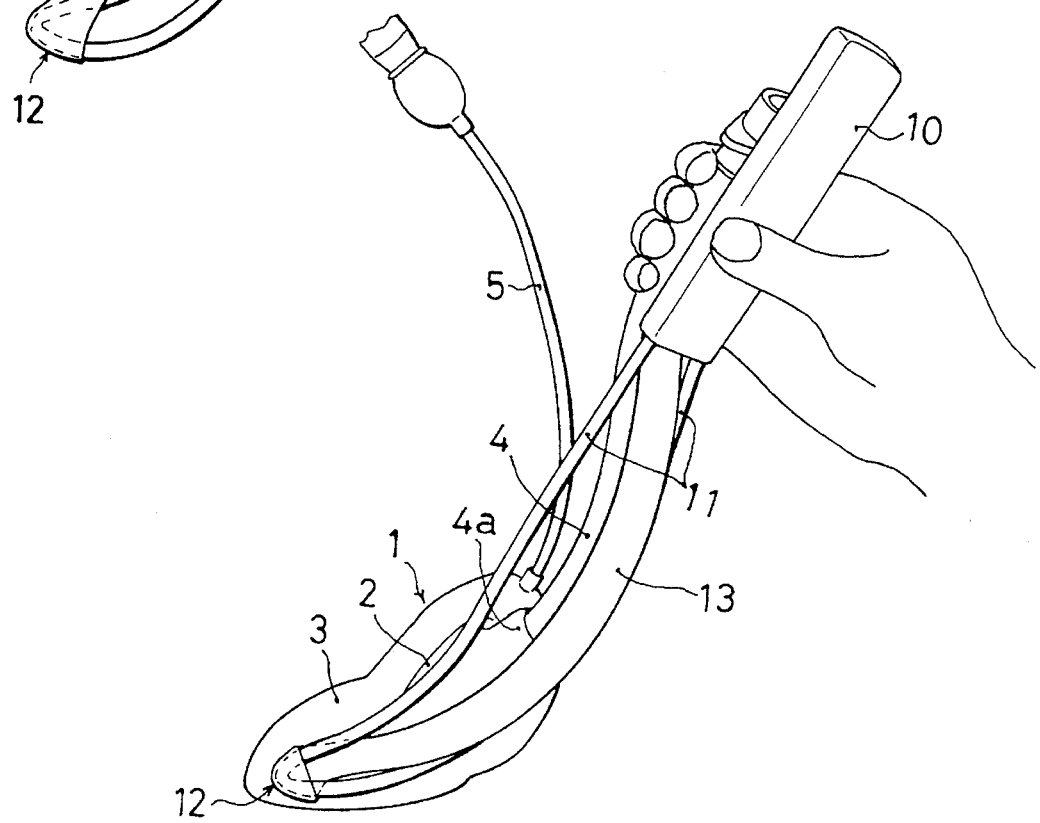

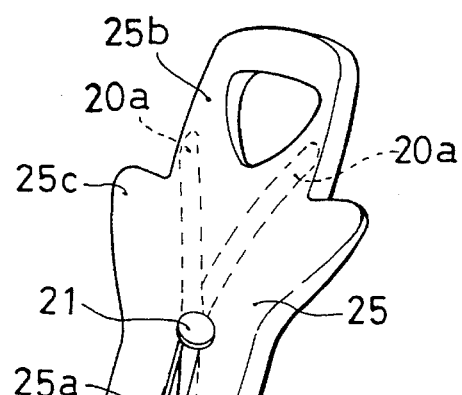
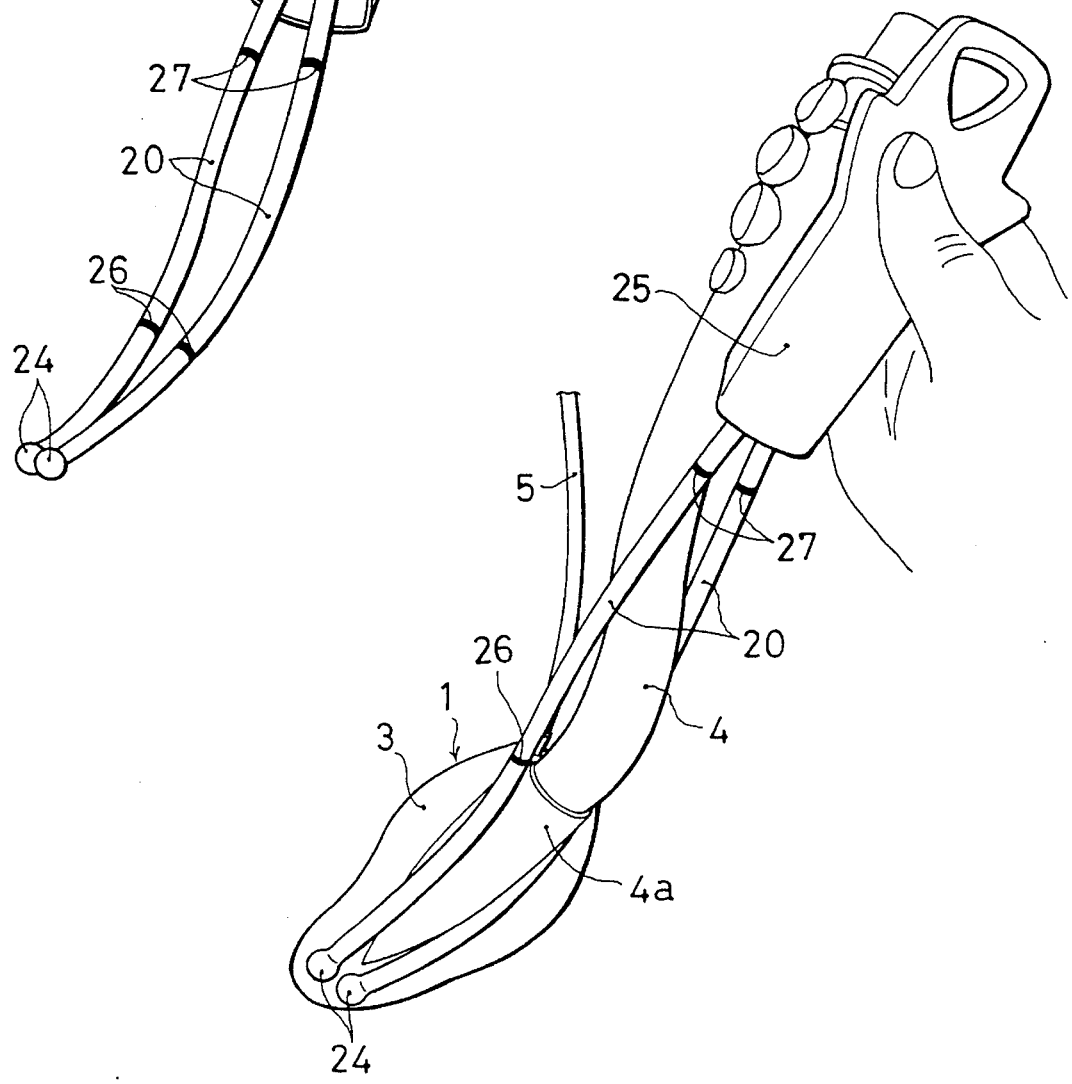

APPARATUS FOR INSERTING LARYNGEAL MASK

BACKGROUND OF THE INVENTION

1. Field of the Invention

The present invention relates to an apparatus for inserting into a larynx of a patient a laryngeal mask which is used in general anesthesia, intensive care, critical care or the like to maintain an airway.

2. Description of Related Art

As a method of maintaining an oral airway in an anesthetic management or the like, there has conventionally been used a method of endotracheal intubation by using a laryngoscope. Recently, as shown in FIG. 1A, there is also known a method of using a laryngeal mask 1 which may simply be inserted into the larynx.

The laryngeal mask 1 is made up of an oval mask body 2 and a hollow cuff 3 which is provided on the periphery of the mask body 2. A respiratory tube 4 is connected to a connecting portion 4a on the outside surface (i.e., the wrong side as opposed to the right side) of the mask. The respiration is performed through the holes 2a which are formed in the mask body 2. A tube 5 for injecting air into the cuff 3 is connected to the cuff 3. In a condition in which the cuff 3 is deflated by extracting air therefrom, the laryngeal mask 1 is inserted into the larynx of a patient. Then, the cuff 3 is inflated by injecting air thereinto. In this manner, an airway is maintained by covering the larynx with the mask 1 as shown in FIG. 1B.

In inserting the laryngeal mask 1 into the larynx, it is normal practice to bend the head of the patient backwards, push the laryngeal mask along his palatine wall to prevent the mask from twisting, and urge the laryngeal mask 1. In order to do so it is necessary to insert fingers of an operator into the patient's oral cavity, resulting in a fear of infection. In addition, for the purpose of preventing infection, it is recommended to use rubber gloves. However, according to the report by the FDA (Food and Drug Administration) of the U.S.A. in July, 1991, the occurrence of allergy through the use of rubber gloves has become a problem. Further, as shown in FIG. 1C, the Duff 3 in the front (i.e., head) end portion of the mask 1 will sometimes be peeled off towards the outside thereof, with the result that the mask 1 can no longer be inserted into the larynx.

Considering the above disadvantages, the present invention has an object of providing an apparatus which can surely insert a laryngeal mask into the larynx without the necessity of inserting the operator's fingers into the patient's oral cavity.

According to the first aspect of the present invention, there is provided an apparatus for inserting a laryngeal mask comprising: a holder portion; a pair of clamp bars which extend forwards from the holder portion and which are adapted to hold therebetween in a pinching manner a tube connecting portion provided on an outside surface of the laryngeal mask, the pair of clamp bars being connected together at their front ends to thereby form an abutment portion which is adapted to abut a front end of the outside surface of the laryngeal mask; and a band piece which extends from the abutment portion along the clamp bars towards the holder portion and which can be pulled towards the holder portion.

In accordance with a second aspect of the present invention, there is provided an apparatus for inserting a laryngeal mask comprising: a pair of clamp bars which are arranged to hold therebetween a tube connecting portion provided on an outside surface of the laryngeal mask; pivoting means for pivotally supporting the clamp bars at approximately intermediate portions thereof such that front ends and rear ends of the clamp bars can respectively move towards and away from each other; and an abutment portion which is formed at the front ends of the clamp bars so as to abut a front end of the outside surface of the laryngeal mask.

When the apparatus according to the first aspect of the present invention is used, the tube connecting portion is first pushed into a space between the clamp bars in a condition in which the band piece is placed in abutment or contact with the outside surface of the tube connecting portion. The abutment portion which is formed by the connected portion at the front ends of the clamp bars is made to abut or to be held against the front end of the outside surface of the laryngeal mask. Then, by holding the holder portion with hand, the laryngeal mask is inserted into the larynx while pinchingly holding between the clamp bars the laryngeal mask at its tube connecting portion. At this time, the abutment portion serves to prevent the front end of the laryngeal mask from peeling or bending towards the outside, thereby ensuring a smooth insertion of the laryngeal mask into the larynx. After the above-described insertion, the band piece is pulled out. According to this operation, the tube connecting portion is forced out from the space between the clamp bars, and the clamp bars can be pulled out or withdrawn while leaving the mask inside the larynx.

When the apparatus according to the second aspect of the invention is used, the pair of clamp bars are closed or moved towards each other while the abutment portion at the front end of each of the clamp bars is brought into abutment or contact with the front end of the outside surface of the laryngeal mask. The laryngeal mask is held at its tube connecting portion in a pinching manner between the clamp bars and is inserted into the larynx in this condition. Thereafter, the clamp bars are opened or moved away from each other and are pulled out while leaving the mask inside the larynx.

Whichever of the above-described apparatuses for inserting the laryngeal mask may be used, the mask body at the front end of the laryngeal mask can be held by the apparatus for inserting the laryngeal mask. Therefore, it becomes possible to control the position of insertion of the mask body at a free will of the operator and, as a result, the ratio of occurrence of abnormally positioning the laryngeal mask can be decreased to a minimum.

Furthermore, since it is not necessary to insert the operator's fingers into the oral cavity of the patient, the chances of infection through contact between the operator and the patient can be decreased. The problem of allergy through the use of rubber gloves can also be solved.

The use of the above-described apparatuses for inserting the laryngeal mask makes it possible to insert the laryngeal mask without bending the head of the patient backwards. The apparatuses can therefore be used to advantage to maintain an airway in case of head injury where the patient's head is difficult of urging backwards.

If the above-described apparatuses for inserting the laryngeal mask are used, it becomes possible even for an unskilled operator to easily insert the laryngeal mask and, furthermore, it becomes possible to insert the laryngeal mask without exerting undue force to it. The frequency in which the mask can be repeatedly used increases and it is therefore very economical.

BRIEF DESCRIPTION OF THE DRAWINGS

The above and other objects and the attendant advantages of the present invention will become readily apparent by reference to the following detailed description when considered in conjunction with the accompanying drawings wherein:

FIGS. 1A through 1C show a laryngeal mask, in which FIG. 1A is a perspective view thereof, FIG. 1B is a side view showing the condition of insertion thereof, and FIG. 1C is a side view showing a condition in which the front end thereof is peeled off or bent towards the outside;

FIG. 2 is a perspective view, as seen from the inside of an apparatus for inserting the laryngeal mask according to the present invention;

FIG. 3 is a perspective view thereof in use, as seen from the outside;

FIG. 6 is a perspective view, as seen from the inside, of still anther embodying example of the present invention apparatus;

FIG. 7 is a perspective view thereof in use, as seen from the outside.

DETAILED DESCRIPTION OF PREFERRED EMBODIMENTS

Figure 4:
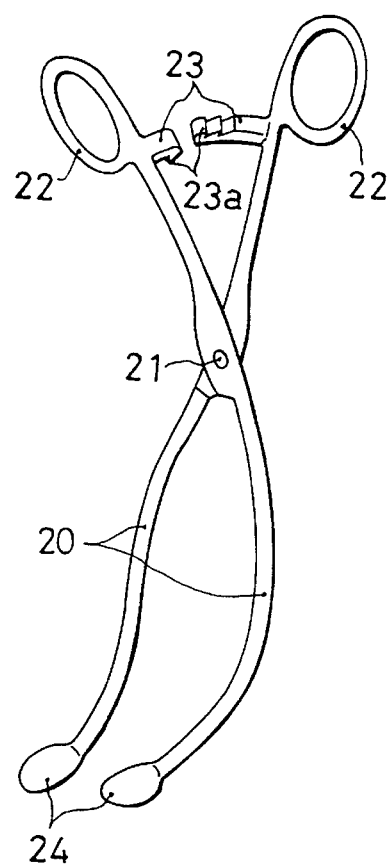
FIG. 4 is a perspective view, as seen from the inside, of another embodying example of the present invention apparatus.

FIG. 2 shows an embodying example of an apparatus for inserting a laryngeal mask of the present invention. This apparatus comprises a holder portion 10 and a pair of clamp bars 11, 11 which extend forwards (i.e., towards the front or head Side) from the holder portion 10. Those portions of the clamp bars 11, 11 which are close to the front ends thereof are bent towards inside (i.e., to the right side as opposed to the wrong side) to suit the bending from a palate through a larynx. The front ends of the clamp bars 11, 11 are connected together. In the present example, a single piece of bar is bent at an intermediate portion to form both clamp bars 11, 11 so that both clamp bars 11, 11 are connected together at the bent portion. However, two pieces of bars may also be connected together at their front ends by welding or the like.

The connected portion at the front ends of both clamp bars 11, 11 is formed into an abutment portion or holding portion 12 which can abut or hold the front end of the outside surface of the laryngeal mask 1. A band piece or a piece of band 13 which is engaged at one end thereof with the abutment portion 12 is provided. A ring 14 is attached to the other end of the band piece 13 such that the ring 14 is engageable with a hook 15 which is provided on the inside surface of the holder portion 10. In the present example, the band piece 13 is made of an elastic material. However, a band piece 13 without elasticity is also acceptable as long as it is provided loosely to allow for pushing a tube connecting portion 4a into the space between the clamp bars 11, 11 as described hereinafter.

Next, a method of using the above-described apparatus for inserting the laryngeal mask will now be explained.

First, in a condition in which a cuff 3 of the laryngeal mask 1 is deflated, the abutment portion 12 is caused to abut the outside surface of the cuff 3 at the front end portion of the mask 1. In a condition in which the tube connecting portion 4a on the outside surface of the mask 1 is brought into contact or abutment, on its outside surface, with the band piece 13, the tube connecting portion 4a is pushed into the space between the clamp bars 11, 11 as shown in FIG. 3.

In so doing, the distance between the clamp bars 11, 11 is broadened and, consequently, the tube connecting portion 4a is held in a pinching manner between the clamp bars 11, 11 through their elastic restoring force. Further, by pushing the tube connecting portion 4a into the space between the clamp bars 11, 11, the front end portion of a tube 4 to be connected to the tube connecting portion 4a protrudes towards the outside by passing through the space between the clamp bars 11, 11. The tube 4 will then come out to the inside at the rear end portion of the tube 4 which is positioned on the inside of the holder portion 10. If an arrangement is made such that the tube 4 is elastically held in a pinching manner between the clamp bars 11, 11 at this portion of coming out to the inside, the laryngeal mask 1 can be held by the clamp bars 11, 11 in a more stable manner.

Thereafter, while holding together the holder portion 10 and the rear end of the tube 4 with a hand, the laryngeal mask 1 is inserted into the larynx of the patient as the laryngeal mask 1 is being held by the clamp bars 11, 11. At this time, even if the cuff 3 at the front end of the laryngeal mask 1 may abut the rear wall of the oral cavity, the cuff 3 will not peel off or be bent towards the outside because this portion is supported on its outside surface by the abutment portion 12. The laryngeal mask 1 can thus securely be inserted into the larynx. Once the laryngeal mask 1 has been inserted, a finger is inserted into or engaged with the ring 14 of the band piece 13 to pull the band piece 13 towards the operator (i.e., away from the abutment portion 12). As a result of this operation, the tube 4 and the tube connecting portion 4a are pushed out by the band piece 13 from the outside through the space between the clamp bars 11, 11. If the holder portion 10 is moved towards the operator in this condition, the clamp bars 11, 11 are pulled out while leaving the laryngeal mask 1 inside the larynx. Then, the cuff 3 is filled with air through the air tube 5 to inflate the cuff 3 to bring it to a condition as shown in FIG. 1B. The operation of insertion is thus completed.

FIG. 4 shows another embodying example of the present invention apparatus. The apparatus is made up into the form of a forceps having a pair of clamp bars 20, 20 which are pivotally supported by a pivot 21 at intermediate portions thereof such that it can be opened or closed, i.e., both ends of the clamps can respectively be moved towards and away from each other.

At a rear end of each of the clamp bars 20, 20, there is formed a finger-engaging portion 22 for use in operation to open or close the clamp bars 20, 20. A hook piece 23 is projectingly provided on a rear internal side of each of the clamp bars 20, 20. It is thus so arranged that, when both clamp bars 20, 20 are closed, claw pieces 23a which are formed on the hook pieces 23, 23 may be engaged with each other to thereby hold the clamp bars 20, 20 in a predetermined closed condition.

Figure 5:
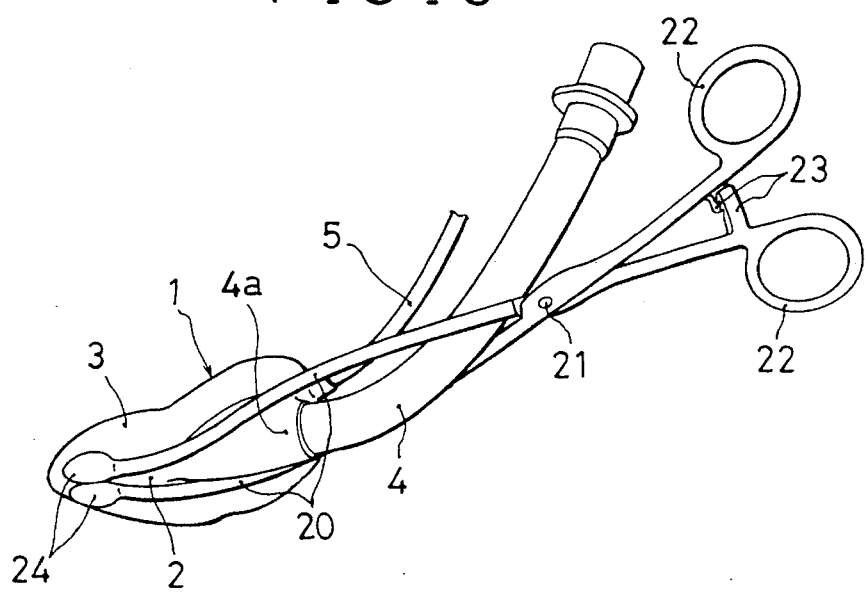
FIG. 5 is a perspective view thereof as seen from the outside.

The portion near the front end of each of the clamp bars 20, 20 is bent towards the inside to suit the bending from the palate through the larynx. Further, at the front end of each of the clamp bars 20, 20, there is formed an abutment portion 24, 24 which can abut or hold the front end of the outside surface of the laryngeal mask 1. The clamp bars 20, 20 are also laterally bent into a form of bowlegs, i.e., into an O-shape so that, as shown in FIG. 5, the tube connecting portion 4a and that portion of the tube 4 which is closer to the rear end thereof may be held in a pinching manner between the clamp bars 20, 20.

In use, the clamp bars 20, 20 are closed in a condition in which they are brought into abutment with the front end of the outside surface of the laryngeal mask 1 to hold the laryngeal mask 1 at its tube connecting portion 4a and the tube 4 between the clamp bars 20, 20. The laryngeal mask 1 is then inserted into the larynx while preventing the cuff 3 at the front end of the laryngeal mask 1 from peeling or bending towards the outside. After the laryngeal mask 1 has been inserted, the clamp bars 20, 20 are opened and pulled out.

FIG. 6 shows a modified embodying example of the apparatus shown in FIG. 4. In this example, in place of the finger-engaging portions 22, 22 and the hooking pieces 23, 23 of FIG. 4, there are provided a hollow holder portion 25. The rear end portions 20a, 20a of the clamp bars 20, 20 are inserted into the hollow holder portion 25 up through the portion at which both are pivotally supported. The pivot 21 is engaged with a slot 25a which is formed in the inside surface of the holder portion 25 such that the holder portion 25 is slidable relative to the clamp, bars 20, 20 with the pivot 21 serving as a guide. A narrow-width portion 25b and a wide-width portion 25c are formed in the rear end and the intermediate portion, respectively, of the holder portion 25. By pushing the rear end portions 20a, 20a of the clamp bars 20, 20 into the narrow-width portion 25b, the clamp bars 20, 20 can be restricted in a closed condition. By pulling the holder portion 25 upwards (i.e., to the rear end side) to thereby move the rear end portion 20a into the wide-width portion 25c, the clamp bars 20, 20 are opened.

The clamp bars 20, 20 may be provided with marks 26, 27 at the front end and the intermediate portion thereof. By this arrangement, if the rear end of the tube connecting portion 4a is made to coincide with the front side mark 26 as shown in FIG. 7, the laryngeal mask 1 can be held in an appropriate positional relationship between the clamp bars 20, 20. Further, if the intermediate mark 27 is made to coincide with a predetermined tooth such as a dog tooth or the like of the patient in inserting the laryngeal mask 1 into the larynx, the inserting position of the laryngeal mask 1 can be adequately controlled.

As can be seen from the above description, according to the present invention, the laryngeal mask can be inserted into the larynx of the patient without inserting the operator's fingers into the oral cavity. Further, the abutment portion at the front end of the laryngeal mask serves to prevent the cuff at the front end of the laryngeal mask from peeling or bending towards the outside. The laryngeal mask can therefore be inserted smoothly and securely.

It is readily apparent that the above-described apparatus for inserting a laryngeal mask meets all of the objects mentioned above and also has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. An apparatus for inserting a laryngeal mask comprising:

a pair of clamp bars which are adapted to hold therebetween a tube connecting portion provided on an outside surface of a laryngeal mask in a holding position;

pivoting means for pivotally supporting said clamp bars at approximately intermediate portions thereof such that front ends and rear ends of said clamp bars can respectively move towards and away from each other; and an abutment portion which is formed at said front ends of said clamp bars so as to be capable of abutting a front end of the outside surface of the laryngeal mask when in said holding position;

said clamp bars being sized and shaped such that in said holding position said clamp bars be capable of fitting into the larynx of a patient with said abutment portion abutting the front of the outside surface of the laryngeal mask, in particular said clamp bars being bent, at a portion towards the front end of said pivoting means, to one side of an axial direction of said pivoting means so as to be capable of fitting into a bent area from the palatum to the larynx of the patient;

whereby said apparatus can hold the laryngeal mask in said holding position to insert the laryngeal mask into the larynx of the patient and can be pivoted open to a releasing position wherein said clamp bars release the tube connecting portion to remove the apparatus.

2. An apparatus for inserting a laryngeal mask according to claim 1, wherein said clamp bars are laterally bent into a form of bowlegs at a portion on the front side of said pivoting means.

3. An apparatus for inserting a laryngeal mask according to claim 1 or 2, wherein said clamp bars are provided at their rear ends with finger-engaging portions for use in moving said clamp bars towards and away from each other and with hook pieces which are arranged to hold said clamp bars in a closed condition.

4. An apparatus for inserting a laryngeal mask, comprising:

a holding portion adapted to be hand held;

a pair of elongated clamp bars extending below said holding portion;

at least one abutment portion formed at an opposite end of said elongated clamp bars from said holding portion;

said elongated clamp bars being spaced apart at an inserting portion, into which a tube connecting portion provided on an outside surface of the laryngeal mask can be inserted, a sufficient distance to pinchingly hold the tube connecting portion;

said elongated clamp bars being sized and shaped such that in said inserting portion said clamp bars are capable of fitting into the larynx of a patient with said holding portion outside of the patient's mouth and with said at least one abutment portion abutting a front end of the outside surface of the laryngeal mask; and means for releasing the pinching hold of said elongated clamp bars in a releasing position when the laryngeal mask has been fully inserted into the patient's larynx;

whereby said clamp bars are capable of holding the laryngeal mask in said inserting portion to insert the laryngeal mask into the larynx of the patient without placing one's hands into the mouth of the patient and without the front end of the laryngeal mask bending back towards the outside, and whereby said clamp bars release the laryngeal mask in said releasing position to remove only the apparatus.

5. The apparatus for inserting a laryngeal mask according to claim 4, wherein said means for releasing includes a pivoting means for pivotally supporting said clamp bars so as to move away from one another.

6. The apparatus for inserting a laryngeal mask according to claim 4, wherein said means for releasing includes a band piece which extends between said clamp bars and which can be pulled so as to push the laryngeal mask from between said clamp bars.

7. A method for maintaining an oral airway, comprising the steps of:

(a) providing an apparatus for inserting a laryngeal mask, comprising:
   a hand held portion (10, 22);
   a pair of elongated clamp bars (11, 20) extending below said hand held portion; and
   at least one abutment portion (12, 24) formed at an opposite end of said elongated clamp bars from said hand held portion;

(b) placing a tube connecting portion (13, 4) between the clamp bars, and placing the abutment portion so as to abut a front end of the outside surface of the laryngeal mask;

(c) while holding the hand held portion by hand inserting the laryngeal mask into the larynx of a patient while the clamp bars hold the laryngeal mask at the connecting tubing and while the abutment portion serves to prevent the front end of the laryngeal mask from bending towards the outside;

(d) separating the connecting tubing and the clamp bars and removing the clamp bars and abutment while leaving the laryngeal mask inside of the larynx.

8. The method of claim 7, wherein said step of providing in part (a) includes providing the clamp bars so as to be pivotably supported on a pivot and providing the hand held portion with finger engaging portions which can be separated so as to pivot the clamp bars, and said step of separating in part (d) includes separating the finger engaging portions so as to separate the clamp bars.

9. The method of claim 7, wherein said step of providing in part (a) includes providing a band piece between the clamp bars, and said step of separating in part (d) includes pulling on the band piece so as to push the tube connecting portion from between the clamp bars.

* * * * *

UNITED STATES PATENT AND TRADEMARK OFFICE
CERTIFICATE OF CORRECTION

PATENT NO.: 5,529,582
DATED : June 25, 1996
INVENTOR(S): FUKUHARA et al.

It is certified that error appears in the above-identified patent and that said Letters Patent is hereby corrected as shown below:

In claim 7, column 7, line 9, "port,ion" should read --portion--.

In claim 7, column 8, line 2, "abutment while" should read --abutment portion while--.

Signed and Sealed this

Third Day of December, 1996

Attest:

BRUCE LEHMAN

Attesting Officer     Commissioner of Patents and Trademarks